United States Patent [19]

Krüger et al.

[11] Patent Number: 5,059,623

[45] Date of Patent: Oct. 22, 1991

[54] SUBSTITUTED CYCLOALKYL- AND HETEROCYCLYL-CARBOXANILIDES

[75] Inventors: Bernd-Wieland Krüger; Klaus Sasse, both of Bergisch-Gladbach; Herman Hagemann; Albrecht Marhold, both of Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 333,481

[22] Filed: Apr. 5, 1989

[30] Foreign Application Priority Data

Apr. 29, 1988 [DE] Fed. Rep. of Germany ....... 3814505

[51] Int. Cl.$^5$ ............................................. A01N 37/18
[52] U.S. Cl. .................................... 514/613; 514/449; 514/452; 514/459; 514/467; 514/471; 514/624; 549/372; 549/378; 549/425; 549/450; 549/487; 549/511; 564/123; 564/189; 564/190; 564/191
[58] Field of Search ............... 564/123, 189, 190, 191; 514/624, 613

[56] References Cited

U.S. PATENT DOCUMENTS

| | | | |
|---|---|---|---|
| 2,654,722 | 10/1953 | Young et al. | 564/123 |
| 3,277,171 | 10/1966 | Hopkins | 564/190 |
| 3,746,765 | 7/1973 | Ruschig et al. | 564/123 |
| 3,772,002 | 11/1973 | Ramello | 430/553 |
| 4,021,224 | 5/1977 | Pallos et al. | 564/189 |
| 4,144,270 | 3/1979 | Neri et al. | 564/190 |
| 4,166,735 | 9/1979 | Pilgram et al. | 71/118 |
| 4,184,867 | 1/1980 | Pilgram et al. | 71/98 |
| 4,447,260 | 5/1984 | Noguchi et al. | 564/190 |
| 4,666,943 | 5/1987 | Naguchi et al. | 514/627 |

FOREIGN PATENT DOCUMENTS

| | | | |
|---|---|---|---|
| 023669 | 2/1981 | European Pat. Off. | 564/123 |
| 0052473 | 5/1982 | European Pat. Off. | |
| 0100615 | 2/1984 | European Pat. Off. | |
| 0116409 | 8/1984 | European Pat. Off. | |
| 0205271 | 12/1986 | European Pat. Off. | |
| 1900202 | 8/1970 | Fed. Rep. of Germany. | |
| 1907117 | 9/1970 | Fed. Rep. of Germany. | |
| 1255161 | 12/1971 | United Kingdom. | |

Primary Examiner—Richard L. Raymond
Assistant Examiner—Scott C. Rand
Attorney, Agent, or Firm—Sprung Horn Kramer & Woods

[57] ABSTRACT

A substituted cycloalkyl- or heterocyclyl-carboxanilide of the formula (I)

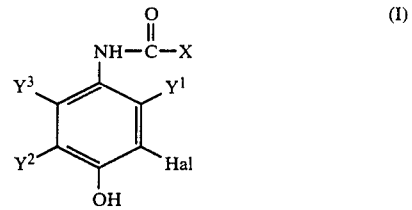

in which
X stands for an unsubstituted or an alkyl-substituted cycloalkyl or an unsubstituted or an alkyl-substituted heterocyclic,
Hal stands for halogen and
$Y^1$, $Y^2$ and $Y^3$ independently of one another stand for hydrogen, halogen, an unsubstituted or a halogen-substituted alkyl, an unsubstituted or a halogen-substituted alkoxy or an unsubstituted or a halogen-substituted alkylthio. Such substituted cycloalkyl- or heterocyclyl-carboxanilides are useful as fungicides.

8 Claims, No Drawings

SUBSTITUTED CYCLOALKYL- AND HETEROCYCLYL-CARBOXANILIDES

The present invention relates to new cycloalkyl-and heterocyclyl-carboxanilides, a process for their preparation and their use for combating pests, in particular fungi.

It is known that certain phenols possess good fungicidal properties (cf. W. Kramer in Pflanzenschutz und Schadlingsbekampfung [Plant Protection and Pest Control], ed. K.-H. Buchel, p. 143 et seq., 1977, Georg Thieme Verlag, Stuttgart, and references cited therein).

Furthermore, many carboxanilides having a fungicidal action, in particular a powerful action against plant pathogens which are tolerant to benzimidazole, have been disclosed (cf. EP 117,024, EP 125,901 and EP 100,615).

New cycloalkyl- and heterocyclyl-carboxanilides of the general formula (I)

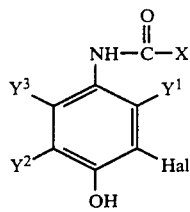

in which
X stands for optionally alkyl-substituted cycloalkyl or an optionally alkyl-substituted heterocyclic,
Hal stands for halogen and
$Y^1$, $Y^2$ and $Y^3$ independently of one another stand for hydrogen, halogen, optionally halogen-substituted alkyl, optionally halogen-substituted alkoxy or optionally halogen-substituted alkylthio,
have been found.

The substituted cycloalkyl- and heterocyclylcarboxanilides of the formula (I) contain one or more centers of asymmetry and can thus be present in the form of diastereomers or diastereomeric mixtures which are obtained in various mixing ratios. Mainly, they are obtained as racemates.

Furthermore, it has been found that the new substituted cycloalkyl- or heterocyclyl-carboxanilides of the formula (I)

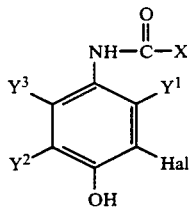

in which
X stands for optionally alkyl-substituted cycloalkyl or an optionally alkyl-substituted heterocyclic,
Hal stands for halogen and
$Y^1$, $Y^2$ and $Y^3$ are identical or different and stand for hydrogen, halogen, optionally halogen-substituted alkyl, optionally halogen-substituted alkoxy or optionally halogen-substituted alkylthio,
are obtained when aminophenols of the formula (II)

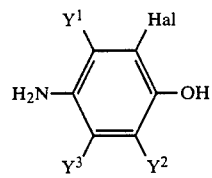

in which
Hal, $Y^1$, $Y^2$ and $Y^2$ have the abovementioned meanings,
are reacted with carboxylic acid derivatives of the formula (III)

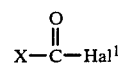

in which
X has the abovementioned meaning and
$Hal^1$ stands for halogen, preferably chlorine, or a leaving group customary in acylation reactions, preferably an activating ester radical, if appropriate in the presence of an acid acceptor and if appropriate in the presence of a solvent or diluent.

Finally, it has been found that the substituted cycloalkyl- and heterocyclyl-carboxanilides of the formula (I) possess, inter alia, a powerful fungicidal activity. The new compounds can also be used in synergistic mixtures with other known, highly active compounds.

Within the scope of the present invention, the substituents can generally have the following meanings.

Unless stated otherwise, halogen can denote fluorine, chlorine, bromine and iodine, preferably fluorine, chlorine and bromine.

Alkyl, alkoxy and alkylthio stand for a radical having 1-6, preferably 1-4 and particularly preferably 1-3, carbon atoms per alkyl unit, for example methyl, ethyl, n- and iso-propyl, n-, sec-, iso- and tert.-butyl, pentyl, n-hexyl or iso-hexyl, methoxy, ethoxy, n- and iso-propoxy, n-, sec.-, iso- and tert.-butoxy, pentoxy and hexoxy, methylthio, ethylthio, n- and iso-propylthio, n-, sec.-, iso- and tert.-butylthio, pentylthio and hexylthio.

Halogenoalkoxy and halogenoalkylthio generally stand for a straight-chain or branched hydrocarbon radical which is linked via oxygen or sulphur and which has 1-6 carbon atoms and 1-9 identical or different halogen atoms. Preferred radicals are those having 1-4 carbon atoms and 1-5 identical or different halogen atoms. Very particularly preferred radicals are those having 1 or 2 carbon atoms and 1-3 identical or different halogen atoms. Examples which may be mentioned are: trifluoromethoxy, trichloromethoxy, difluorochloromethoxy, dichlorofluoromethoxy, difluoroethoxy, trifluoroethoxy, tetrafluoroethoxy, pentafluoroethoxy, trifluoromethylthio, trichloromethylthio, difluorochloromethylthio, dichlorofluoromethylthio, difluoroethylthio, trifluoromethylthio and tetrafluoroethylthio.

Halogenoalkyl has the meaning of halogenoalkoxy.

Cycloalkyl generally stands for a cyclic hydrocarbon radical having 3-10 carbon atoms. Preferred radicals are those having 3-7 carbon atoms. Examples which may be mentioned are: cyclopropyl, cyclobutyl, cyclopentyl, cyclohexyl, cycloheptyl and cyclodecanyl.

The cycloalkyl radicals can be monosubstituted to polysubstituted. Substituents which may be mentioned are alkyl having 1-6 carbon atoms.

Alkyl has the preferred and particularly preferred meaning which has already been mentioned above.

Heterocyclic can stand for a radical having 4-7 ring members, preferably 4-6 ring members, containing one or more hetero atoms, such as oxygen, sulphur or nitrogen, in addition to carbon. 5- or 6-Rings having one or two of the hetero atoms mentioned, above all oxygen, are preferred. Examples which may be mentioned are: oxetanyl, oxolanyl, oxanyl, dioxolanyl and dioxanyl. The heterocyclics can be monosubstituted to polysubstituted by identical or different alkyl substituents having 1-6, preferably 1-4 and particularly preferably 1 or 2 carbon atoms. Examples which may be mentioned are: 3-methyl-oxetan-3-yl, 2-methyl-oxolan-2-yl, 2-methyl-oxan-2-yl, 5-methyl-1,3-dioxolan-5-yl, 2-ethyl-oxolan-2-yl, 2-ethyl-oxan-2-yl and 5-ethyl-1,3-dioxolan-5-yl.

Formula (I) provides a general definition of the substituted cycloalkyl- and heterocyclyl-carboxanilides according to the invention. Preferred compounds of the formula (I) are those where X stands for cyclopropyl, cyclobutyl, cyclopentyl, cyclohexyl or cycloheptyl, each of which is optionally monosubstituted to tetrasubstituted by identical or different, straight-chain or branched alkyl substituents having 1-4 carbon atoms, or for a heterocyclic having 4-6 ring members containing one or two identical or different hetero atoms, such as oxygen or nitrogen, in addition to carbon. The heterocyclic can be monosubstituted to hexasubstituted by identical or different, straight-chain or branched alkyl substituents having 1-4 carbon atoms, Hal stands for fluorine, chlorine or bromine, $Y^1$, $Y^2$ and $Y^3$ are identical or different and stand for hydrogen, fluorine, chlorine, bromine, straight-chain or branched alkyl having 1-4 carbon atoms, straight-chain or branched alkoxy or alkylthio, each having 1-4 carbon atoms, or for halogenoalkyl, halogenoalkoxy or halogenoalkylthio, each having 1-4 carbon atoms in the straight-chain or branched alkyl moiety and having 1-5 identical or different halogen atoms.

Particularly preferred compounds of the formula (I) are those in which

X stands for cyclopropyl, cyclobutyl, cyclopentyl cyclohexyl or cycloheptyl, each of which is monosubstituted or disubstituted by identical or different, straight-chain or branched alkyl substituents having 1-3 carbon atoms, for oxanyl, oxolanyl, dioxanyl, dioxolanyl or oxetanyl, each of which is optionally monosubstituted or disubstituted by identical or different, straight-chain or branched alkyl substituents having 1-3 carbon atoms, $Y^1$, $Y^2$ and $Y^3$ are identical or different and stand for hydrogen, fluorine, chlorine, bromine, methyl or trifluoromethyl and Hal stands for fluorine, chlorine or bromine.

Very particularly preferred compounds of the formula (I) are those where

X stands for cyclopropyl, cyclobutyl, cyclopentyl, cyclohexyl or cycloheptyl, each of which is substituted in the 1-position by methyl or ethyl and each of which is additionally substituted by another alkyl radical having 1-3 carbon atoms, Hal stands for fluorine, chlorine or bromine and $Y^1$, $Y^2$ and $Y^3$ are identical or different and stand for hydrogen, fluorine, chlorine, bromine or trifluoromethyl.

If, for example, 2,6-dichloro-4-amino-phenol and 1-methyl-1-chlorocarbonylcyclohexane are used as starting substances, the course of the reaction can be represented by the following equation:

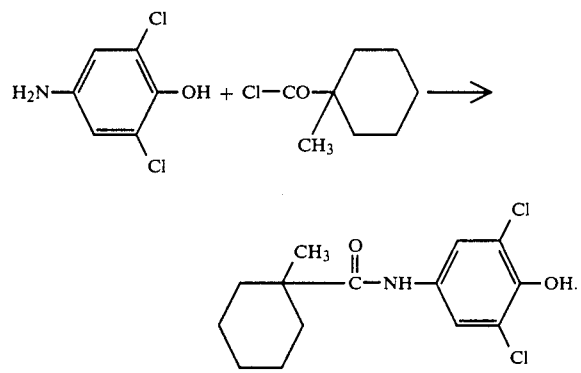

Formula (II) provides a general definition of the aminophenols required as starting substances for carrying out the process according to the invention. In this formula (II), the radicals Hal and $Y^1$–$Y^3$ have the meanings which have already been indicated in connection with the description of the compounds of the formula (I) according to the invention. The majority of the compounds are known and can be prepared by analogous processes (cf. "Methoden der organischen Chemie" [Methods of Organic Chemistry], Houben-Weyl, vol. VI/1c, Phenols, part 1, Georg Thieme Verlag, Stuttgart, 1976, and "Reaktionen der organischen Synthese" [Reactions in Organic Synthesis], Cesare Ferri, p. 81, 89, 91, 97, 118, 120, 122, 124, 126, 128, Georg Thieme Verlag, Stuttgart, 1978).

The 4-amino-2-chloro- or -2-bromo-6-trifluoromethylphenols are known from Jp. Kokai Tokkyo Koho Jp 61/126055 and, for example, 4-amino-2,3,5,6-tetrafluorophenol from Zh. Org. Khim. 10(9), 1923-1927 (1974). The compounds of the formula (II A)

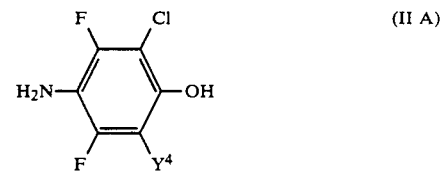

in which $Y^4$ stands for fluorine or chlorine are still new and form the subject-matter of a German Application P 3,804,288, which has not yet been prior-published, by the applicant, and they can be prepared, for example, from corresponding hydroxybenzoic acids of the formula (VA)

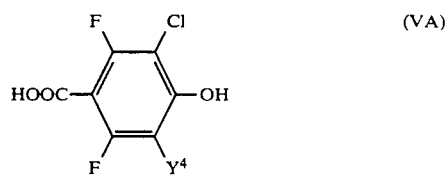

by decarboxylation and subsequent nitration of the resulting phenols of the formula (VI A)

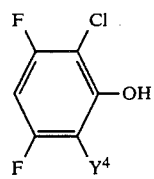

to give the nitro compounds of the formula (VII A)

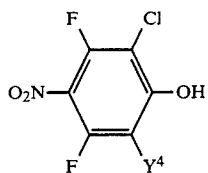

which are then hydrogenated, for example, using hydrogen and Raney nickel, to give the corresponding amines of the formulae (II A).

The compounds of the formula (VII A) are also still new and form the subject-matter of the above non-prior-published German application.

Formula (III) in which X stands for cycloalkyl provides a general definition of the cycloalkanecarboxylic acid derivatives also required for carrying out the process according to the invention. In this formula (III), the radicals X and Hal¹ have the meanings already given in connection with the description of the compounds of the formula (I) according to the invention. The compounds are known and can be prepared by analogous processes (cf. Diversi et. al., Synthesis 1971, 258; US 3,674,831; "Reaktionen der organischen Synthese" [Reactions in Organic Synthesis], Ceasare Ferri, p. 460, 461, 1978, Georg Thieme Verlag, Stuttgart). Formula (III) in which X stands for heterocycyl also provides a definition of the heterocyclic carboxylic acid derivatives additionally required for carrying out the process according to the invention. The compounds are known (cf. DE 1,900,202; DE 2,212,641) and can be prepared by analogous processes.

If appropriate, the process according to the invention is carried out in the presence of acid acceptors. Acid acceptors which may be used are all customary acid-binding agents. Alkali metal carbonates and alkali metal alkoxides, such as sodium carbonate, potassium carbonate, sodium methoxide, potassium methoxide, sodium ethoxide and potassium ethoxide, furthermore aliphatic, aromatic and heterocyclic amines, for example triethylamine, trimethylamine, dimethylaniline, 1,8-diazabicyclo(5,4,0)-undec-7-ene, dimethylbenzylamine and pyridine, have proved particularly useful.

To carry out the process according to the invention, 1-2 moles, in particular 1-1.4 moles, of the compounds of the general formula (III) are preferably employed per mole of aminophenol of the general formula (II).

Suitable diluents for carrying out the process according to the invention are virtually all inert organic diluents. In particular, these include aliphatic and aromatic, optionally halogenated hydrocarbons, such as pentane, hexane, heptane, cyclohexane, petroleum ether, benzine, ligroin, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

In general, the process according to the invention is carried out at temperatures between −50° C. and 120° C. The range between 0° C. and 110° C. is preferred. In general, the reactions are carried out under atmospheric pressure.

Working up is carried out by customary methods, for example by extracting the products from the reaction mixture, which has been diluted with water, using toluene or methylene chloride, washing the organic phase with water, drying and distilling or so-called "incipienly distilling", i.e. heating for a relatively long time at moderately increased temperatures under reduced pressure, in order to free it from the last volatile constituents, or by purifying by chromatography over silica gel, or for example by crystallization. The compounds are characterized by the refractive index, melting point, $R_f$ value or boiling point.

The active compounds according to the invention are suitable for use in combating pests, in particular for use as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bacterial agents are used in plant protection for combating Psuedomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestois* pv. oryzae; Pseudomonas species, such as, for example, *Pseudomonas syringae* pv. lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example,

*Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine encapsulations in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products. As dispersing agents there are suitable, for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering; spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

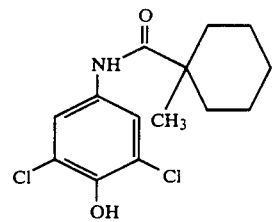

18.5 g (0.085 mol) of 4-amino-2,6-dichlorophenol are dissolved in 150 ml of tetrahydrofuran, and 8.6 g (0.085 mol) of triethylamine are added, followed at 0° C. by 15 g (0.094 mol) of 1-methylcyclohexanecarbonyl chloride. The mixture is stirred overnight at 20° C., and another 5 g of carbonyl chloride and another 2.8 g of triethylamine are added to the reaction mixture to complete the reaction. After 2 hours, the mixture is poured onto ice, and the solid which has been filtered off with suction is recrystallized from toluene. The abovementioned compound of melting point 140° C. is obtained; yield: 22.3 g (=87% of theory).

The compounds of the formula (I) are obtained analogously:

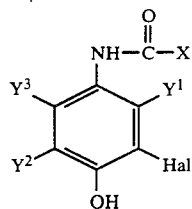

(I)

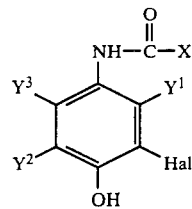

(I)

| Example No. | X | Hal | Y¹ | Y² | Y³ | Physical data |
|---|---|---|---|---|---|---|
| 2 | cyclohexyl-CH₃ | Cl | H | H | H | |
| 3 | " | Cl | Cl | H | H | m.p. 141° C. |
| 4 | " | Cl | F | F | F | m.p. 138° C. |
| 5 | cyclopentyl-CH₃ | Cl | H | Cl | H | |
| 6 | cyclobutyl-CH₃ | Cl | H | Cl | H | |
| 7 | cyclopropyl-CH₃ | Cl | H | Cl | H | m.p. 167° C. |
| 8 | cyclohexyl-CH₃ | Cl | H | Cl | H | |
| 9 | dioxane-C₂H₅ | Cl | H | Cl | H | |
| 10 | dioxane-CH₃ | Cl | H | Cl | H | |
| 11 | cyclohexyl(CH₃)(C₃H₇-i) | Cl | H | Cl | H | m.p. 77–81° C. |
| 12 | tetrahydropyran-CH₃/O | Cl | H | Cl | H | |
| 13 | oxetane-CH₃ | Cl | H | Cl | H | |
| 14 | (CH₃)₂C(O)(O)C(CH₃) | Cl | H | Cl | H | |
| 15 | cyclopropyl-CH₃ | Cl | Cl | H | H | |
| 16 | cyclobutyl-CH₃ | Cl | Cl | H | H | |
| 17 | cyclopentyl-CH₃ | Cl | Cl | H | H | |
| 18 | cycloheptyl-CH₃ | Cl | Cl | H | H | |
| 19 | cyclohexyl-CH₃ | F | Cl | H | F | |
| 20 | cyclohexyl-CH₃ | F | F | Cl | F | |
| 21 | cyclohexyl-CH₃ | F | F | H | H | |
| 22 | cyclohexyl-CH₃ | Br | Br | H | H | |

-continued

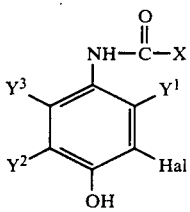

| Example No. | X | Hal | Y¹ | Y² | Y³ | Physical data |
|---|---|---|---|---|---|---|
| 23 | ![cyclohexyl-CH3] | Cl | F | Cl | F | |
| 24 | ![cyclohexyl-CH3] | F | Cl | Cl | F | |

PREPARATION OF THE STARTING COMPOUNDS

Example A1

3,5-Dichloro-2,6-difluoro-4-hydroxybenzoic acid 300 g of potassium hydroxide, 600 ml of water, 15 g of tetrabutylammonium chloride and 135 g of 3,5-dichloro-2,4,6-trifluorobenzotrifluoride are initially introduced into a stirred apparatus, and the mixture is then refluxed for 5 hours. When the reaction is complete, the mixture is cooled and acidified by dropwise addition of hydrochloric acid. The solid is filtered off with suction and dried in vacuo. Yield: 93 g of melting point 102°–105° C.

Example A2

3-Chloro-2,5,6-trifluoro-4-hydroxy-benzoic acid

In analogy to Example A1, 238 g of product of melting point 87°–90° C. are obtained by refluxing 400 g of NaOH, 1200 ml of water, 15 g of tetraethylammonium chloride and 276 g of 3-chloro-tetrafluorobenzotrifluoride for 6 hours.

Example A3

2,6-Dichloro-3,5-difluorophenol 50 g of 3,5-dichloro-2,6-difluoro-4-hydroxy-benzoic acid and 10 ml of dimethylformamide are mixed and heated. At 105°–130° C., carbon dioxide evolves, and the reaction is allowed to proceed to completion at this temperature. 200 ml of toluene and 80 ml of water are then added in succession, the phases are separated, and the organic phase is dried and then distilled. 34 g of the product of a boiling point of 87°–88° C. and refractive index of $n_D^{20}$: 1.5310 are obtained.

Example A4

In analogy to Example A3, 2-chloro-3,5,6-trifluorophenol of boiling point 68°–70° C./20 mbar is obtained.

Example A5

2,6-Dichloro-3,5-difluoro-4-nitro-phenol 20 g of 2,6-dichloro-3,5-difluorophenol are initially introduced into 70 ml of acetic acid, and 8 g of 98% strength nitric acid are added dropwise. Subsequently, the mixture is then stirred for 2 hours at room temperature, taken up in 150 ml of dichloromethane and washed twice with water. 18 g of product remain after distilling off the dichloromethane. 94% pure in accordance with GC analysis.

Example A6

2-Chloro-3,5,6-trifluoro-4-nitrophenol

In analogy to Example A5, 25 g of 2-chloro-3,5,6-trifluoro-4-nitrophenol of a purity of 93% and a melting point of 107°–109° C. are obtained by nitrating 28 g of 2-chloro-3,5,6-trifluorophenol.

Example A7

2,6-Dichloro-3,5-difluoro-4-amino-phenol 18 g of 2,6-dichloro-3,5-difluoro-4-nitrophenol are hydrogenated in 100 ml of methanol in the presence of 1.5 g of Raney nickel at 25°–45° C. under 30–50 bar of hydrogen until hydrogen is no longer taken up. After filtration, the solution is freed from the solvent under reduced pressure. 13 g of aminophenol (GC purity 98.4%) remain; m.p. 151° C.

Example A8

2-Chloro-3,5,6-trifluoro-4-amino-phenol

In analogy to Example A7, 20 g of aminophenol (GC purity 97%) are obtained by hydrogenating 25 g 2-chloro-3,5,6-trifluoro-4-nitro-phenol in 120 ml of methanol and 2 g of Raney nickel.

Use Examples

In the following Use Example, the known fungicidal compound of the formula A

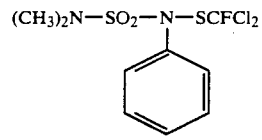

N,N-dimethyl-N-phenyl-N'-(fluorodichloromethylthio)-sulphamide [K. H. Buchel "Pflanzenschutz und Schadlingsbekampfung" [Plant Protection and Pest Control], Georg Thieme Verlag, Stuttgart, p. 141 (1977)] is used as a comparison substance.

Example

Botrytis test (bean)/protective

Solvent: 4.7 parts by weight of acetone
Emulsifier: 0.3 part by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after inoculation, the size of the infected spots on the leaves is evaluated.

In this test, for example the compounds of Preparation Examples 1 and 3 show a clearly superior activity compared with the prior art.

It will be appreciated that the instant specification and examples are set forth by way of illustration and not limitation, and that various modifications and changes may be made without departing from the spirit and scope of the present invention.

What is claimed is:

1. A cycloalkyl- or carbox-anilide of the formula

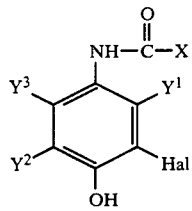
(I)

wherein

X stands for cyclopropyl which is substituted in the alpha position, cyclobutyl, cyclopentyl, cyclohexyl or cycloheptyl, each of which is unsubstituted or monosubstituted to tetrasubstituted by identical or different, straight-chain or branched alkyl substituents having 1–4 carbon atoms, Hal stands for fluorine, chlorine or bromine, $Y^1$, $Y^2$ and $Y^3$ independently of one another stand for hydrogen, fluorine, chlorine, bromine, straight-chain or branched alkyl having 1–4 carbon atoms, for straight-chain or branched alkoxy or alkylthio, each having 1–4 carbon atoms per alkyl moiety, or for halogenoalkyl, halogenoalkoxy or halogenoalkylthio, each having 1–4 carbon atoms in the straight-chain or branched alkyl moiety and having 1–5 identical or different halogen atoms.

2. A substituted cycloalkyl- carboxanilide according to claim 1 wherein

X stands for cyclopropyl, cyclobutyl, cyclopentyl cyclohexyl or cycloheptyl, each of which is monosubstituted or disubstituted by identical or different, straight-chain or branched alkyl substituents having 1–3 carbon atoms, $Y^1$, $Y^2$ and $Y^3$ independently of one another stand for hydrogen, fluorine, chlorine, bromine, methyl or trifluoromethyl and Hal stands for fluorine, chlorine or bromine.

3. A substituted cycloalkyl- carboxanilide according to claim 1, wherein

X stands for cyclopropyl, cyclobutyl, cyclopentyl, cyclohexyl or cycloheptyl, each of which is substituted in the 1-position by methyl or ethyl and each of which can be substituted by another straight-chain or branched alkyl radical having 1–3 carbon atoms, Hal stands for fluorine, chlorine or bromine and $Y^1$, $Y^2$ and $Y^3$ independently of one another stand for hydrogen, fluorine, chlorine, bromine or trifluoromethyl.

4. A substituted cyclo-alkyl- carboxanilide according to claim 1 selected from the group consisting of

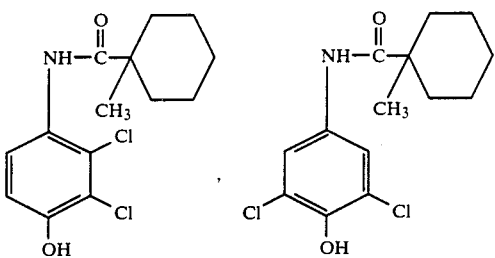

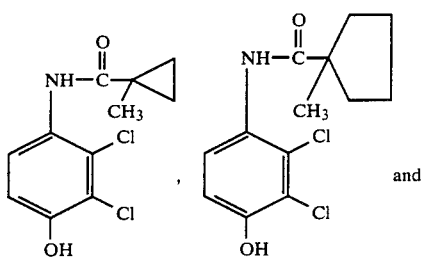

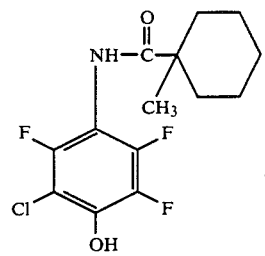

5. A substituted cycloalkyl-carboxanilide according to claim 1 selected from the group consisting of

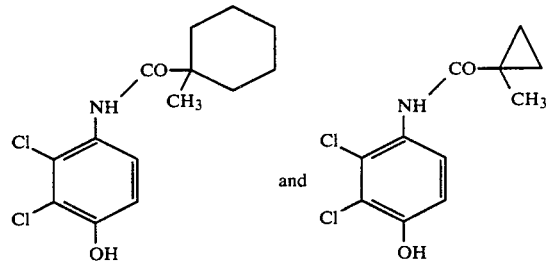

6. A fungicidal composition comprising a fungicidally effective amount of a substituted cyclo-alkyl- carboxanilide according to claim 1 in admixture with a diluent.

7. A method of combating fungi comprising applying to said fungi or to a locus from which it is desired to exclude said fungi a fungicidally effective amount of a substituted cyclo-alkyl- carboxanilide according to claim 1.

8. A method according to claim 7, wherein the cycloalkyl- carboxanilide is selected from the group consisting of

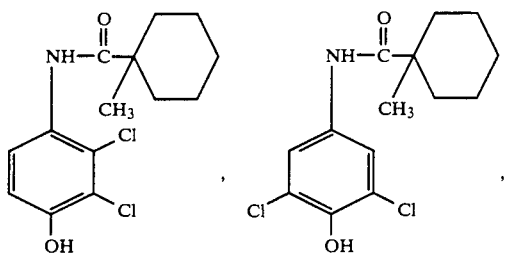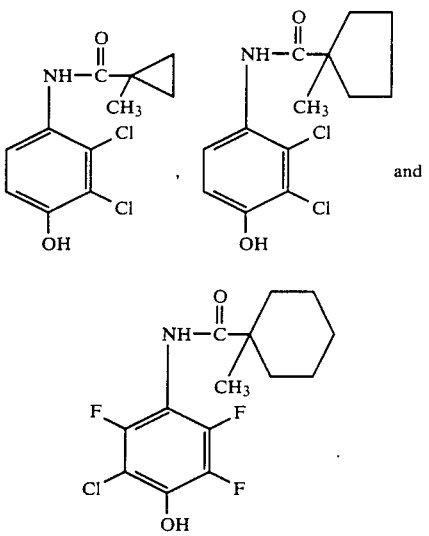
* * * * *